Figure 1:
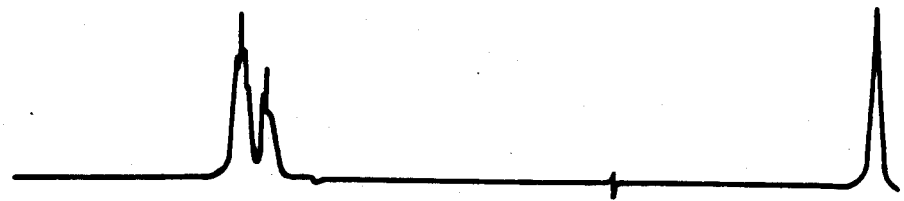
Figure 1:
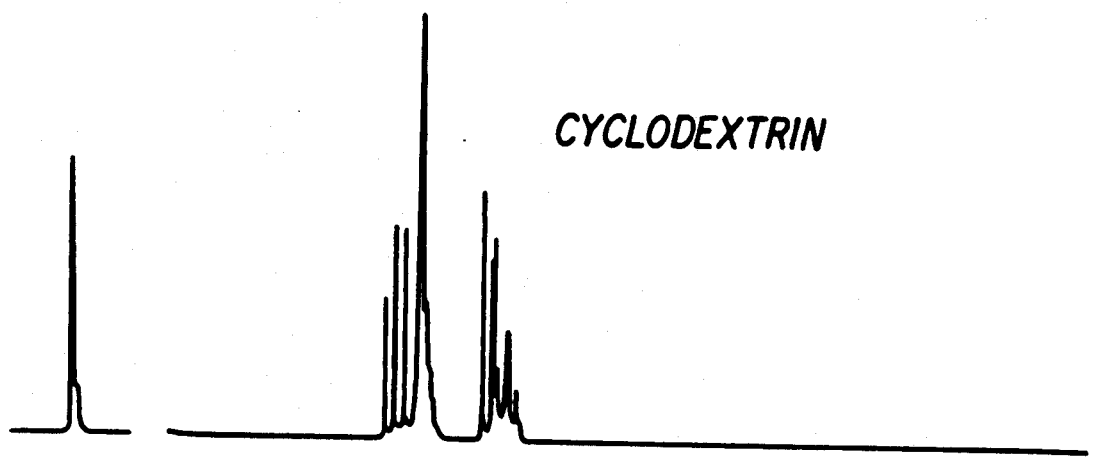
Figure 1:
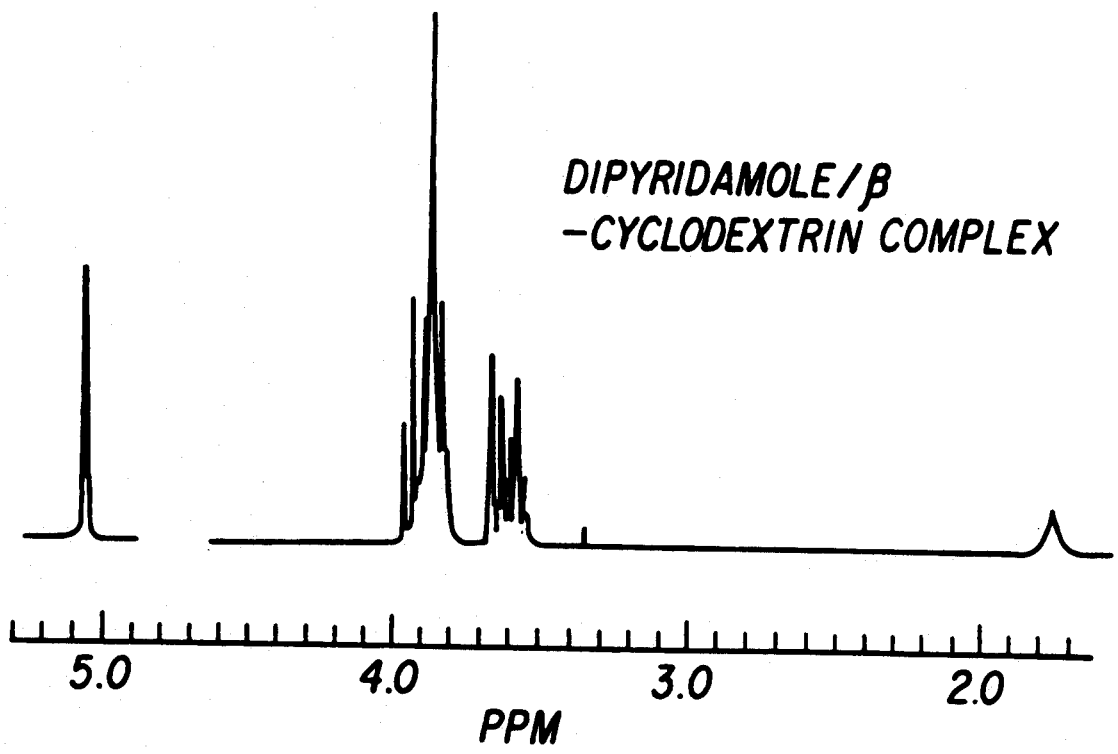

United States Patent [19]

Fregnan et al.

[11] Patent Number: 5,010,064
[45] Date of Patent: Apr. 23, 1991

[54] INCLUSION COMPLEXES OF DIPYRIDAMOLE WITH CYCLODEXTRINS

[75] Inventors: Giancarlo Fregnan, Milan; Guido Vandoni, Correzzana; Giangiacomo Torri, Milan, all of Italy

[73] Assignee: Edmond Pharma s.r.l., Milan, Italy

[21] Appl. No.: 201,038

[22] Filed: Jun. 1, 1988

[30] Foreign Application Priority Data

Jun. 17, 1987 [IT] Italy ................... 20925 A/87

[51] Int. Cl.⁵ ............... A01N 43/40; A61K 31/715; C08B 37/16
[52] U.S. Cl. ........................ 514/58; 514/258; 536/103
[58] Field of Search ............... 514/58, 258; 536/103

[56] References Cited

U.S. PATENT DOCUMENTS

| | | | |
|---|---|---|---|
| 4,054,736 | 10/1977 | Hayashi et al. | 536/103 |
| 4,228,160 | 10/1980 | Szejtli et al. | 424/180 |
| 4,438,106 | 3/1984 | Wagu et al. | 514/58 |
| 4,518,588 | 5/1985 | Szejtli et al. | 514/58 |
| 4,565,807 | 1/1986 | Uekama et al. | 514/58 |
| 4,603,123 | 7/1986 | Chiesi et al. | 514/58 |

FOREIGN PATENT DOCUMENTS 082754 1/1982 Japan.
2104907 7/1982 United Kingdom.

OTHER PUBLICATIONS

Kaneto Uekama: Inclusion Complexes of Cyclodextrins With Organic Drug Molecules (The Japanese Journal of Antiobiotics-Dec. 1979, pp. 103-110).
G. E. Hardee et al., Microcalorimetric Investigations of Pharmaceutical Complexes (Acta Pharm. Suec. 15, 188-199 (1978).
J. Pitha et al, "Hydroxypropyl-$\beta$-Cyclodextrin: Preparation and Characterization; Effects on Solubility of Drugs," International Journal of Pharmaceutics, vol. 29 (Mar., 1986), pp. 73-82.

*Primary Examiner*—John W. Rollins
*Assistant Examiner*—Gary L. Kunz
*Attorney, Agent, or Firm*—Stevens, Davis, Miller & Mosher

[57] ABSTRACT

Inclusion complexes of dipyridamole with beta cyclodextrins in the molar ratio of dipyridamole to cyclodextrin ranging from 1:1 to 1:12 provides higher and more consistent blood concentrations than can be achieved by the dipyridamole alone.

6 Claims, 1 Drawing Sheet

INCLUSION COMPLEXES OF DIPYRIDAMOLE WITH CYCLODEXTRINS

The present invention relates to new compounds obtained by complexing 2,2',2",2"'-(4,8-dipiperidinopyrimido/5,4,d/-pyrimidine-2,6-diyldinitrilo)tetraethanol (also called dipyridamole) with cylodextrins or dimethylcyclodextrins of α, β and γ type.

Dipyridamole is a compound endowed with platelet aggregation inhibiting properties, antithrombotic and vasodilator properties used in the cardiac, cerebral and renal pathology due to increased platelet aggregation capacity, in the coronary deficiency either accompanied or not with anginous crisis, in the prophylaxis of myocardial infarction and in cardiopathies as coadjuvant of the digitalis therapy.

It is known that dipyridamole is poor soluble in water at a pH higher than 5.5-6 (UK Patent No. 807,826); furthermore, it is not well adsorbed and shows blood levels different from one to another subject and for repeated administrations in the same subject. On the other hand, to be active as platelet aggregation inhibiting agent, the compound must cause blood levels in the man higher than 1 mcg/ml, but not higher than 2.0-2.5 mcg/ml, in that it might show some side effects, such as cephalea and nausea. Inclusion complexes of cyclodextrins with some organic molecules have been already described in the literature (Eur. Pat. Appln. No. 0153 998; U.S. Pat. No. 4,438,106).

It has been now found that dipyridamole gives inclusion complexes with α, β and γ cyclodextrins (natural cyclic substances consisting of 6, 7 and 8 units of glucopyranose respectively) or with dimethylcyclodextrins (prepared in laboratorium by selective methylation of natural substances) and it has been found that complexes thus obtained are endowed with a greater stability, high solubility, are quicker adsorbed and better tolerated than dipyridamole.

Thus, according to one of its aspects, the present invention relates to inclusion complexes of dipyridamole with α, β or γ cyclodextrins.

Generally, in the complexes of the present invention the molar ratio dipyridamole: cyclodextrin may vary from 1:10 to 1:1, advantageously from 1:1.3 to 1:6, preferably from 1:2.5 to 1:5.

Among cyclodextrins, the β-cyclodextrin is particularly indicated.

According to another of its aspects, the present invention relates to a process for the preparation of the above mentioned inclusion complexes. The process can be practically performed according to one of the following procedures:

the dipyridamole is directly stirred in an aqueous solution of cyclodextrins, the complex is separated and dried by lyophilization, by heating in vacuo or by atomization in hot air stream or, the dipyridamole is directly stirred in an aqueous solution of cyclodextrins made strongly acidic (e.g. by HCl or formic acid) and the complex is separated by lyophilization, atomization in hot air stream or drying by heating in vacuo, or the dipyridamole is dissolved in organic solvents (ethanol, chloroform), is stirred with cyclodextrins dissolved in water; the complex contained in the aqueous phase is separated by centrifugation and is dried by lyophilization or heating in vacuo. The thus obtained complex shows always properties more favourable than dipyridamole.

The examples described hereinafter illustrate the invention but do not represent in any way a limitation of the same.

EXAMPLE 1

1 g of dipyridamole is dispersed in 100 ml of a 2% aqueous solution of β-cyclodextrin (2 g in all) and thereafter is kept under strong agitation at 37° C. for 9-12 hr. At the end, the whole is cooled to room temperature, is filtered off and the clear solution is lyophilized.

EXAMPLE 2

417 mg of dipyridamole are soludispersed in 100 ml of a 2.5% aqueous solution of β-cyclodextrin (1.5 g in all); the whole is stirred at 45° C. for 2 hr. and thereafter at room temperature for further 9-20 hr. Then, the whole is lyophilized.

EXAMPLE 3

2 g of dipyridamole are soludispersed in 50 ml of a 13% aqueous solution of dimethyl-β-cyclodextrin (6.5 g in all). The soludispersion is stirred for 5-12 hr. by keeping it at the temperature of 45° C. At the end, the whole is cooled to room temperature, is filtered off and the clear solution is lyophilized.

EXAMPLE 4

100 mg of dipyridamole are soludispersed in 10 ml of a 1.3% aqueous solution of β-cyclodextrin (130 mg in all). The whole is stirred for 9-12 hr. at room temperature and is filtered off. The clear solution is dried by heating it in vacuo at 60°-70° C.

EXAMPLE 5

1 g of dipyridamole is soludispersed in 50 ml of a 10% aqueous solution of γ-cyclodextrin (5 g in all); the whole is heated at 60° C. and is kept at this temperature for 9-12 hr., under stirring. After having cooled to room temperature, the whole is filtered off and the aqueous solution is lyophilized.

EXAMPLE 6

250 ml of a 1% solution of β-cyclodextrin (2.5 g in all) are added to 500 mg of dipyridamole; the whole is agitated at room temperature for 9-12 hr. and is dried by atomization in air stream heated at 120° C.

EXAMPLE 7

20 liters of a 1.25% aqueous solution of β-cyclodextrin (250 g in all) are acidified with formic acid to pH 2. Under strong stirring and after having raised the temperature to 60° C., powdered dipyridamole (50 g) and a further amount of formic acid are added until the compound is completely dissolved (the final pH of the solution is kept at 3).

After 2 hr. the heating is interrupted and the solution is kept under stirring for further 7 hr. Thereafter, the whole is dried by atomization in air stream at 120° C.

EXAMPLE 8

1 g of dipyridamole and 5 g of β-cyclodextrin are very carefully mixed.

Slowly, while stirring, 100 ml of water heated to 60° C. are poured and a 2N solution of hydrochloric acid is added to have a final pH=2.5. The whole is stirred for further 6 hr. and then it is dried by atomization in air stream at 120° C.

EXAMPLE 9

375 mg of dipyridamole are dissolved in 100 ml of chloroform. The chloroform solution is then strongly stirred with 100 ml of a 1.5% aqueous solution of β-cyclodextrin (1.5 g in all) for 24 hours, at room temperature. At the end the organic phase is separated from the aqueous phase by centrigugation at 1000 rpm, for 10 minutes. The aqueous phase is separated and is dried by lyophilization.

EXAMPLE 10

400 mg of dipyridamole are dissolved in 20 ml of ethanol and strongly stirred with 100 ml of a 1% aqueous solution of β-cyclodextrin (1 g in all) for 24 hr, at room temperature. Thereafter, the whole is dried at 60°-70° C., in vacuo.

EXAMPLE 11

1500 mg of dipyridamole are dissolved in 50 ml of ethanol and strongly stirred with 50 ml of a 15% solution or soludispersion of α-cyclodextrin (7.5 g in all) for 24 hr, at room temperature. The crystalline precipitate is separated by filtration and is dried at 55°-60° C., in vacuo.

Quantitative Determination of Dipyridamole Contained in the Complex (PREPARED ACCORDING TO EXAMPLES FROM 1 TO 11)

100 mg of the inclusion complex are dissolved in 100 ml of phosphate buffer ph 5.5.

The undissolved portion is removed by filtration and in the suitably diluted filtrate, the quantity of dipyridamole existing is measured by spectrophotometry at 284 nm.

Characterization of the Inclusion Complex (PREPARED AS DESCRIBED IN EXAMPLE 7) by $^1$H-NMR Analysis The solutions of β-cyclodextrin (β-CD) and of dipyridamole complex/β-cyclodextrin, are prepared by dissolving 5 mg and 3 mg respectively in 0.5 ml of 99.8% $D_2O$ (deuterium oxide). The dipyridamole solution is prepared by dissolving 3 mg in 0.5 ml of $D_2O$ at pH 3.0.

Solutions are evaporated under reduced pressure, treated with an equal volume of $D_2O$ three times and then analysed by means of a Bruker Spectrometer CXP-300 (300 MHz) in Fourier's transformation. As it appears from FIG. 1, the spectrum of dipyridamole/β-cyclodextrin shows, when compared with the spectrum of single components, a significant variation of the chemical shift, corresponding to 7.5 MHz, of the signal corresponding to the proton in position 3 of the β-cyclodextrin (3.93 ppm). An analogous variation is observed on the proton 5 of the β-cyclodextrin (3.83 ppm) but it cannot be measured because of the superimposition of signals of some dipyridamole protons ($CH_2$ close to heteroatoms). These differences are those expected in the formation of complexes due to the penetration of guest molecules in the hydrophobic cavity of cyclodextrins. The ratio between the β-cyclodextrin and dipyridamole in the various preparations is calculated by the ratio between the integrals of the anometric signal of the β-cyclodextrin (7H, 5.06 ppm) and of the signal corresponding to the aliphatic —$CH_2$— of dipyridamole (12H, 1.77 ppm). In one typical preparation (the preparation described in example 7) this molar ratio is 3 (6.7 w/W).

SOLUBILITY OF THE INCLUSION COMPLEX

As example, a typical experiment is hereinafter described. 10 g of the dipyridamole/β-cyclodextrin complex (prepared according to the procedure described in example 7), 2 g of dipyridamole and 2 g of dipyridamole mixed with 8 g of lactose have been introduced into separate vessels containing 50 ml of of phosphate buffer (pH 5.5) and have been stirred for 30 minutes at room temperature.

The three samples have been then filtered off and clear solutions have been read by means of the spectrophotometer at 284 nm after suitable dilution.

It has been observed that the solution of the complex contains a quantity of dipyridamole 4.5 and 4 times higher than the other solutions.

PHARMACOLOGIC ACTIVITY

Hereinafter some experiments are described carried out on animal to evaluate the pharmacologic activity of the complexed compound (prepared according to the procedure described in example 7) in comparison with the pharmacologic activity of non-complexed dipyridamole or of dipyridamole dispersed in lactose.

(A) PLATELET AGGREGATION INHIBITING ACTIVITY EX VIVO

New Zealand whitish female rabbits (average body weight 3.2 kg) have been treated with capsules containing 30, 60 and 120 mg/kg respectively of the complex dipyridamole/β-cyclodextrin, or 10 and 20 mg/kg os respectively of dipyridamole, or 60 and 120 mg/kg os respectively of dipyridamole dispersed in lactose (in the ratio 1:5 b.w.).

0, 0.5, 1, 2 and 4 hours after the treatment, 4.5 ml of blood have been drawn from the left ear vein of the animals, in the presence of 0.5 ml of 3.8% trisodium citrate as anticoagulant.

The platelet rich plasma (PRP) has been separated by centrifugation for 10 minutes and has been suitable diluted to have always 250,000–300,000 platelet/$mm^3$ with plasma free of platelets (obtained from blood samples by further centrifugation for 10 minutes at 3200 rpm.

The platelet aggregation has been measured by the turbidimetric method under continuous stirring at 37° C., after having added ADP (Adenosine diphosphate to PRP (1.5 μg/ml).

Results reported in Table 1 clearly show that complexing gives rise to an aggregation inhibiting activity more precociuos and more intense (with a ratio of at least 3:1) and that when dipyridamole is dispersed in an inert excipient, such as lactose, its activity is not affected.

TABLE 1

Platelet aggregation inhibiting activity of dipyridamole included in stable complexes with β-oyclodextrin (β-CD). Experiment ex vivo in platelet rich plamsa of rabbits treated per os.

| Substance | Dose mg/kg os | No of treated rabbits | % platelet aggregation at various times (hr) after drawing of venous blood | | | | |
|---|---|---|---|---|---|---|---|
| | | | 0 | 0.5 | 1 | 2 | 4 |
| dipyridamole/β-CD | 30* | 5 | 85 ± 2.8 | 49 ± 1.8 | 45 ± 2.1 | 43 ± 1.7 | 59 ± 1.9 |
| | 60* | 5 | 78 ± 2.9 | 33 ± 1.7 | 26 ± 0.98 | 28 ± 1.0 | 48 ± 1.6 |
| | 120* | 5 | 84 ± 3.2 | 24 ± 2.1 | 13 ± 1.1 | 15 ± 0.97 | 39 ± 1.4 |
| dipyridamole | 10 | 5 | 83 ± 3.0 | 63 ± 3.7 | 44 ± 3.2 | 40 ± 2.9 | 49 ± 2.7 |
| | 20 | 4 | 87 ± 3.2 | 58 ± 5.9 | 29 ± 4.1 | 27 ± 3.8 | 38 ± 3.9 |
| dipyridamole/lactose | 60* | 4 | 80 ± 2.7 | 60 ± 4.8 | 42 ± 2.9 | 41 ± 3.2 | 52 ± 3.1 |
| | 120* | 4 | 87 ± 3.1 | 57 ± 3.4 | 28 ± 3.6 | 29 ± 3.7 | 40 ± 2.8 |

*The dose relates to the dipyridamole/β-cyclodextrin complex or to the dipyridamole-lactose mixture (both with a weight ratio 1:5)

(B) VASODILATOR, HYPOTENSIVE AND HEART ACTIVITY

Beagle dogs (male; average body weight 10.8 kg) have been anesthetized with pentobarbital by i.v. (30-40 mg/kg) and the breast was aseptically opened after having started the artificial respiration by means of a pump.

A magnetic "probe" has been placed around the circumflex coronary artery and a second magnetic "probe" around the left common carotid artery. The wound has been sutured; animals have been allowed to awake and have been treated with antibiotics for 5 days. 1-20 Days after the surgical operation, animals wake and trained to remain layed on a carpet, have been pharmacologically treated by oral route while recording coronary and carotic arterious flows. Contemporarily, by the sfygmomanometric method the arterious pressure has been measured from the tail and the heart frequency. The dipyridamole/β-cyclodextrin complex and dipyridamole in lactose have been administered in capsules at doses corresponding to 2, 4 and 8 mg/kg of the active component. Each animal has been used several times with an interval of at least two days between a treatment and the successive one; each animal received only one single dose and one drug only during the day of the experiment. Data obtained have been summarized in Table 2. By comparing results there is observed that complexing with cyclodextrins favoured the various activities considered in that peak effects relating to systemic arterial pressure, heart frequency, coronary and carotid flow appeared with a remarkable advance and the recorded changes are undoubtedly larger.

mental scheme in "cross over". This means that all animals, 16 hours fasting, received with an interval of a week both a capsule of dipyridamole/β-cyclodextrin and a tablet of commercial dipyridamole containing 75 mg of the active ingredient.

Drawings have been carried out at the following times: 0, 10, 20, 30, 45, 60, 90, 120, 150, 180, 240, 300 and 360 minutes after the treatment. Incidental side effects have been also reported, which have appeared within 24 hours. The blood has been collected in the presence of eparine (10 U.I./ml) and the plasma, separated by centrifugation, has been immediately frozen and stored at −20° C. until extraction. After about 10-20 days of storage, 0.2 ml of plasma has been drawn from each sample and mixed for 15 seconds with 0.5 ml of NaOH 1N. Thereafter, 4 ml of terbutylmethylether have been added and the whole has been stirred for 1 minute. In order to separate the aqueous phase from the organic phase the whole has been centrifuged for 5 minutes. The organic phase has been then removed and dried to dryness under nitrogen stream. The residue has been treated with 100 μl of the mobile phase (methanol-$H_2O$ (65:35) containing 0.005 M of the sodium salt of the 1-heptanesulfonic acid with 0.1% acetic acid) and all or a portion of this volume has been injected into a high pressure liquid chromatograph equipped with a column of the type "reversed phase" and with a fluorometer. An excitation wave length of 285 nm has been chosen in connection with an emission filter of 470 nm.

In Table 3 the concentrations of dipyridamole are reported, measured in the plasma; in Table 4 the corresponding calculated pharmacocinetic parameters are reported.

The complex dipyridamole/β-CD results more bi-

TABLE 2

Cardiovascular activity of dipyridamole included in β-cyclodextrin or dispersed in lactose evaluated in wake dog treated by oral administration.

| Substance | Dose mg/kg os | No. of treated dogs | % of variations towards the pre-treatment period at the moment of the highest response on the following parameters: | | | |
|---|---|---|---|---|---|---|
| | | | Arterious pressure | Heart frequency | Coronary flow | Carotid flow |
| dipyridamole/ β-cyclodextrin | 2 | 3 | −5(37) | 0 | +50(32) | +40(34) |
| | 4 | 4 | −12(35) | −4(43) | +65(33) | +58(38) |
| | 8 | 3 | −15(33) | −8(40) | +106(36) | +98(32) |
| dipyridamole/ lactose | 2 | 3 | −3(68) | 0 | +24(69) | +25(67) |
| | 4 | 3 | −6(69) | 0 | +48(76) | +43(66) |
| | 8 | 2 | −10(78) | −5(85) | +69(84) | +61(75) |

*in dipyridamole as base
Number reported in parentheses indicate the time in minutes necessary to have the peak effect.

(C) BIOAVAILABILITY AND PHARMACOCINETIC

Studies have been carried out on Beagle dogs (male and female; body weight 10-11 kg) following an experioavailable than commercial dipyridamole and shows more precocious and higher blood levels of the active ingredient. Furthermore, adsorption appears to be more constant in each animal, as it is clear when observing standard errors of means calculated for blood concentrations at various times; these standard errors are less. This result is very important because it is known that also in the man a remarkable variability exists as to the adsorption. Furthermore, it is well known that the therapeutic index of dipyridamole is very limited, in that with blood levels higher than 2-2.5 $\gamma$/ml dipyridamole can show undesired side effects (such as cephalea and nausea) and with blood levels lower than 0.5-1 $\gamma$/ml dipyridamole does not result pharmacologically active.

All the above clearly shows that the described invention has a particular therapeutic interest attributed to its better bioavailability, to the higher and quicker activity and to the lower number of side effects.

according to the generally used technique. These tablets have the following composition:
complex of example 7: 450 mg
magnesium stearate: 4 mg
sodium amidoglycolate: 11 mg

EXAMPLE 14

By working as described in example 12, each tablet containing 900 mg of the complex of example 7 is covered with 100 mg of acid resistant methacrylic polymers.

By this way, gastro-resistant tablets are obtained containing 150 mg of dipyridamole.

TABLE 3

Blood levels of dipyridamole measured in dogs after administration by oral route of capsules of dipyridamole/$\beta$-cyclodextrin and of commerical dipyridamole, containing 75 mg of active ingredient.

| Substance | No. dogs | Average plasma concentrations ± S.E. at the following times (minutes): | | | | | | | | | | | | |
|---|---|---|---|---|---|---|---|---|---|---|---|---|---|---|
| | | 0 | 10 | 20 | 30 | 45 | 60 | 90 | 120 | 150 | 180 | 240 | 300 | 360 | 420 |
| dipyridamole/$\beta$-cyclodextrin | 8 | 0 | 0.050 ±0.017 | 0.286 ±0.051 | 3.898 ±0.520 | 6.235 ±0.980 | 6.362 ±0.952 | 6.239 ±0.837 | 6.018 ±0.512 | 5.099 ±0.695 | 2.130 ±0.236 | 1.815 ±0.238 | 1.016 ±0.153 | 0.523 ±0.098 | 0.325 ±0.056 |
| dipyridamole | 8 | 0 | 0.008 ±0.002 | 0.024 ±0.012 | 0.784 ±0.326 | 1.618 ±0.435 | 2.835 ±0.971 | 3.962 ±0.924 | 4.711 ±1.529 | 4.727 ±1.248 | 2.930 ±0.873 | 1.968 ±0.566 | 1.291 ±0.742 | 0.628 ±0.261 | 0.360 ±0.197 |

TABLE 4

Pharmacocinetic parameters calculated in dog after administration by oral route of capsules of dipyridamole/$\beta$-cyclodextrin and of tablets of commercial dipyridamole, containing 75 mg of active ingredient.

| Parameters | | Dipyridamole/$\beta$-cyclodextrin | Commercial dipyridamole |
|---|---|---|---|
| t½$\beta$ | h | 1.23 | 1.32 |
| C max | $\mu$g/ml | 6.718* | 3.822 |
| t max | h | 1.11* | 1.60 |
| AUC(0-7 hr) | $\mu$g/ml/hr | 18.611* | 14.602 |
| K abs. | $h^{-1}$ | 2.45* | 1.24 |
| K el. | $h^{-1}$ | 0.59 | 0.62 |
| Tot. clearance | ml/min | 51.01* | 45.00 |

*$p < 0.05$ dipyridamole/$\beta$-cyclodextrin versus commercial dipyridamole.

Furthermore, the present invention relates to pharmaceutical compositions containing as active ingredient the dipyridamole complexed with cyclodextrins and mixed with suitable pharmaceutically acceptable excipients.

Pharmaceutical forms can be administered either by oral route or by parenteral or by rectal route as capsules, tablets, granulates etc. The unit dose of the active ingredient in the above mentioned forms may vary from 10 to 300 mg for twice or many times a day. Some examples are reported to illustrate the pharmaceutical compositions without limiting them in any way.

EXAMPLE 12

Tablets of 930 mg containing 150 mg of dipyridamole are prepared according to known methods using the complex of example 7. These tablets have the following composition:
complex of example 7: 900 mg
magnesium stearate: 8 mg
sodium amidoglycolate: 22 mg

EXAMPLE 13

Tablets of 465 mg containing 75 mg of dipyridamole are prepared starting from the complex of example 7,

EXAMPLE 15

By working as described in example 13, each tablet containing 450 mg of the complex according to example 7 is covered with 60 mg of acid-resistant methacrylic polymers. Thus, gastro-resistant tablets are obtained, containing 75 mg of dipyridamole.

EXAMPLE 16

900 g of the complex of example 7, 22 g of sodium amidoglycolate, 8 g of magnesium stearate, 50 g of powdered orange flavour and 3.9 kg of saccharose are intimately mixed; the mixture is granulated and the thus obtained granulate is introduced into 1000 sachets. Thus, 1000 dose units are obtained, containing 150 mg of dipyridamole.

EXAMPLE 17

450 g of the complex according to example 7, 60 g of sodium amidoglycolate, 15 g of magnesium stearate, 50 g of powdered orange flavour and 3.425 kg of saccharose are intimately mixed; the mixture is granulated and the thus obtained granulate is introduced into 1000 sachets. By this way, 1000 dose units containing 75 mg of dipyridamole are obtained.

EXAMPLE 18

4.5 g of the complex according to example 7, 25 g of magnesium stearate and 135 g of sodium amidoglycolate are intimately mixed and 5000 capsules are then filled with the obtained mixture. By this way, capsules containing 150 mg of dipyridamole are obtained.

EXAMPLE 19

By working as described in example 8, from 4.5 Kg of the complex of example 7, 10,000 capsules are prepared containing 75 mg of dipyridamole/$\beta$-cyclodextrin in the molar ratio 1:3.

EXAMPLE 20

10,000 Suppositories containing 150 mg of dipyridamole as active ingredient are prepared by adding 9 kg of the complex according to example 7 to 21 kg of a mass for suppositories consisting of solid semi-synthetic glycerides (or polyethyleneglycols, or esters of fatty acids of polyoxyethylenesorbitan or polyoxyethylenestearates), suitably molten, by intimately mixing the whole and pouring into suitable molds.

Obviously, the present invention is not limited to the now described forms and whatever modification can be introduced without going out from limits of the same invention.

We claim:

1. A compound obtained by complexing dipyridamole with beta-cyclodextrin in the molar ratio dipyridamole:cyclodextrin between 1:1 and 1:12 respectively.

2. A compound according to claim 1, wherein the molar ratio dipyridamole:cyclodextrin varies from 1:1 and 1:10.

3. A compound according to claim 1, wherein the molar ratio dipyridamole:cyclodextrin is between 1:1.3 and 1:6.

4. A compound according to claim 1, wherein the molar ratio dipyridamole:cyclodextrin is between 1:2.5 and 1:5.

5. A pharmaceutical composition comprising as active ingredient an inclusion complex according to any of claims from 1 to 4 in unit dosage form.

6. A pharmaceutical composition according to claim 5, comprising the dipyridamole in a quantity from 10 to 300 mg per unit dosage.

* * * * *